March 15, 1955 W. KORDES Plant Pat. 1,362
ROSE PLANT
Filed June 14, 1954
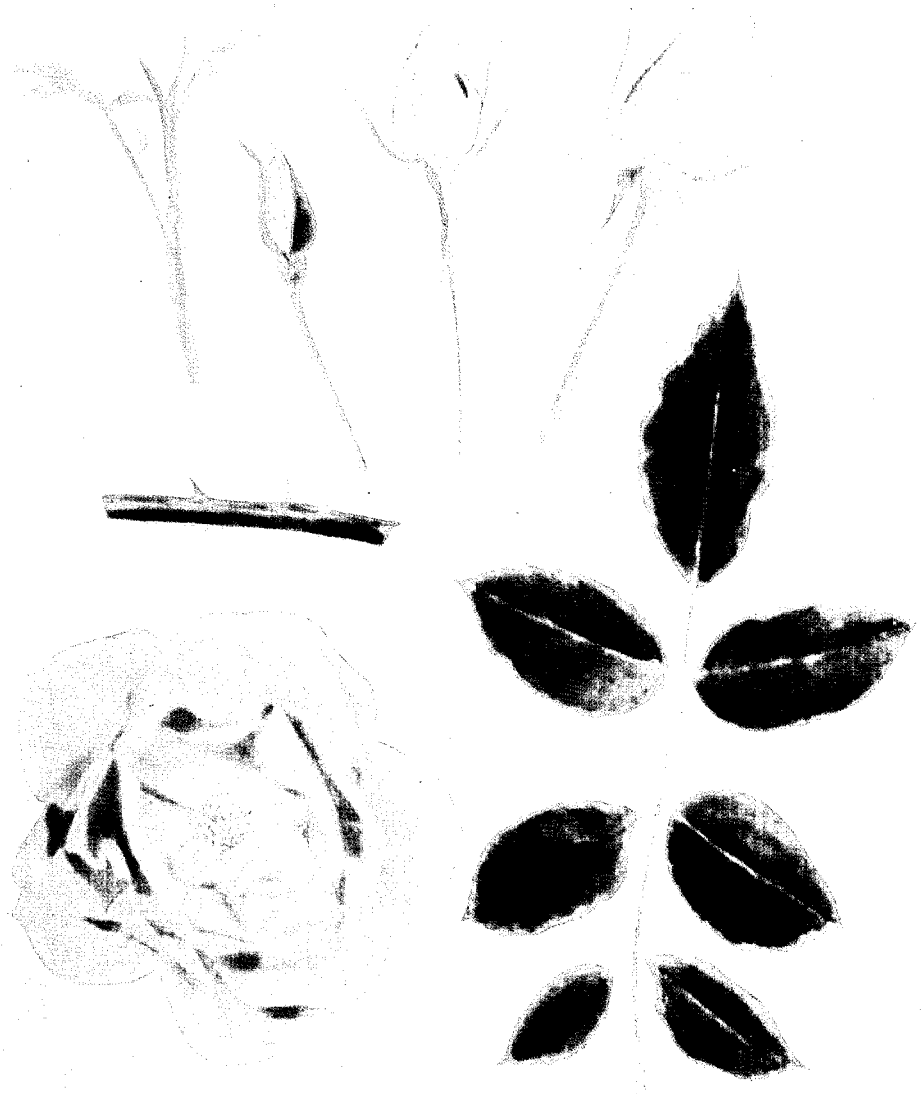
Inventor.
Wilhelm Kordes
By: Robert Cobb
Attorneys.

United States Patent Office

Plant Pat. 1,362
Patented Mar. 15, 1955

1,362

ROSE PLANT

Wilhelm Kordes, near Elmshorn, Holstein, Sparrieshoop, Germany, assignor to Jackson & Perkins Company, Newark, N. Y., a corporation of New York Application June 14, 1954, Serial No. 436,753

1 Claim. (Cl. 47—61)

The present invention relates to a new and distinct variety of rose plant of the large-flowered polyantha class, which was originated by me by crossing the variety "World's Fair" (Plant Patent No. 362) with the variety "Hamburg" (unpatented).

The primary objective in making this cross was to improve the floribunda variety "World's Fair" by instilling more vigor and bushiness into the plants, while at the same time, retaining the flowering qualities of "World's Fair." This objective was fully achieved, as evidenced by the fact that the new variety is particularly characterized by its abundant production of buds and flowers in large, massive heads borne on vigorous and upright plants, the habit of remaining constantly in color throughout the growing season, and the distinctive Dark Red general color tonality of the flowers. More particularly speaking, the petals of the flowers of my new variety are Spectrum Red, with the upper half of the petals at the center of the flower lightly overcast with Rose Red and lightened by a White eye at the base of the petals and offset by the Light Green foliage of the plant, thereby presenting a very different and striking appearance as compared with other rose varieties.

Asexual reproduction of my new variety by budding at Newark, New York, U. S. A., and also at Pleasanton, California, U. S. A., shows that the foregoing characteristics and distinctions come true to form and are established and transmitted through succeeding propagations.

The accompanying drawing shows typical specimens of the flowers, stems and foliage of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—"World's Fair."
*Pollen parent.*—"Hamburg."
Classification:
*Botanic.*—Large-flowered polyantha.
*Commercial.*—Floribunda.

FLOWER (Observations made from specimens grown outdoors at Newark, New York, U. S. A., in the early part of the month of August, and in the early morning.)

Blooming habit: Recurrent—continuous.
Bud:
*Size.*—Medium.
*Form.*—Ovoid; is not affected by wet or hot weather.
*Color.*—When sepals first divide—Pomegranate Purple, Plate 12. When petals begin to unfurl—Nopal Red, Plate 1, lightly overcast with Spectrum Red, Plate 1. When half blown: inside of petals—Carmine, Plate 1; reverse of petals—Scarlet Red, Plate 1, lightly overcast with Spectrum Red, Plate 1.
*Sepals.*—Serrated; slightly branched; curl back when petals begin to unfurl. Color: inside—Kildare Green, Plate 31; outside—Light Elm Green, Plate 17.
*Calyx.*—Color—Biscay Green, Plate 17. Shape—pear. Size—small. Aspect—smooth. Odor when rubbed—none.

*Peduncle.* — Length — medium. Aspect — rough. Strength—erect; slender. Color—Lettuce Green, Plate 5.
*Opening.*—Opens up well; is not affected by adverse weather conditions.
Bloom:
*Size.*—Medium. Average size when fully expanded —3 inches.
*Borne.*—In clusters with large, rounded massive heads.
*Stems.*—Medium length; normal strength.
*Form (when first open).*—Cupped. Permanence—retains its form to the end.
*Petalage.*—Double (full but open center). Number of petals under normal conditions—from 30 to 35.
*Color.*—Center of flower—Spectrum Red, Plate 1, with the upper half of the petals lightly overcast with Rose Red, Plate 12, and with a White, Plate 53 eye at the base of the petals. Outer petals—Scarlet Red, Plate 1, lightly overcast with Rose Red, Plate 12 on the outer edges of the petals. Base of petals (aiglet)—Sulphur Yellow, Plate 5. Inside of petals—Spectrum Red, Plate 1. Reverse of petals—Pomegranate Purple, Plate 12, lightly overcast with Rose Red, Plate 12. General tonality from a distance—Spectrum Red, Plate 1.
*Discoloration.*—General tonality at end of first day —Spectrum Red, Plate 1. Second day—Spectrum Red, Plate 1. Third day—Spectrum Red, Plate 1, lightly overcast with Scarlet Red, Plate 1.
Petals:
*Texture.*—Thick; is not affected by wet or hot weather.
*Appearance.*—Inside—satiny. Outside—shiny.
*Form.*—Oval.
*Arrangement.*—Irregular.
*Petaloids in center.*—Few; small.
*Persistence.*—Drop off cleanly.
*Fragrance.*—Moderate. Nature—tea (average hybrid tea scent).
*Lasting quality.*—On the plant—long. As cut flowers—long.

GENITAL ORGANS

Stamens, anthers: Medium size; many; regularly arranged around styles. Color—Ochraceous Salmon, Plate 15.
Stamens, filaments (threads): Short. Color—Clear Dull Green-Yellow, Plate 17.
Pollen: Color—Pale Ochraceous Salmon, Plate 15.
Styles: Columnar; uneven length; medium length; thin.
Stigmas: Color—Pale Green Yellow, Plate 5.
Ovaries: All enclosed in calyx.
Hips: None.
Seeds: None.

PLANT

Form: Bush.
Growth: Vigorous; upright; compact.
Foliage: 5 to 7 leaflets.
*Size.*—Medium.
*Quantity.*—Normal.
*Color.*—New foliage: upper side—Biscay Green, Plate 17, with the edges Light Vinaceous Cinnamon, Plate 29; under side—Cosse Green, Plate 5. Old foliage: upper side—Hellebore Green, Plate 17; under side—Light Elm Green, Plate 17.
*Shape.*—Oval pointed.
*Texture.* — Upper side — leathery. Under side—smooth.
*Ribs and veins.*—Ordinary.
*Edge.*—Serrated (saw-toothed).
*Serration.*—Both double and single; small.
*Leaf stem.*—Color—Light Cress Green, Plate 31. Under side—prickles.
*Stipules.*—Medium length; bearded.
Wood:
*New wood.* — Color — Lettuce Green, Plate 5. Bark—smooth.
*Old wood.*—Color—Cress Green, Plate 31. Bark—smooth.

Thorns:

*Thorns.*—Quantity: on main stalks from base—few; on laterals from stalk—few. Form—narrow base; medium length; hooked upward. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the vigorous and upright habit of growth of the plant, the abundant production of its flowers in large, massive heads, its habit of remaining constantly in color throughout the growing season, and the distinctive Spectrum Red general color tonality of its flowers, the petals at the center of the flowers having their upper half lightly overcast with Rose Red color and having a White eye at the base of the petals which lightens the color effect thereof and emphasizes the contract with the Light Green foliage of the plant.

No references cited.